United States Patent [19]

Short et al.

[11] Patent Number: 4,600,723

[45] Date of Patent: Jul. 15, 1986

[54] METHOD FOR MINIMIZING DISTURBANCES IN CIRCADIAN RHYTHMS OF BODILY PERFORMANCE AND FUNCTION

[75] Inventors: Roger V. Short, Glen Waverley; Stuart Armstrong, Abbotsford, both of Australia

[73] Assignee: Monash University, Clayton, Australia

[21] Appl. No.: 611,677

[22] Filed: May 18, 1984

[30] Foreign Application Priority Data

May 18, 1983 [AU] Australia ............................... PF9418
Apr. 27, 1984 [AU] Australia ............................... PG4737

[51] Int. Cl.⁴ .......................................... A61K 31/40
[52] U.S. Cl. .................................................. 514/416
[58] Field of Search ........................ 424/274; 514/416

[56] References Cited

FOREIGN PATENT DOCUMENTS 55-5763  4/1980  Japan .

OTHER PUBLICATIONS

Chemical Abstract, 96, 156305w.
Merck Index, 1983, p. 828, No. 5634.
Arendt, J. and Marks, V., "Physiological Changes Underlying Jet Lag", *British Medical Journal*, 16 Jan. 1982, pp. 144–146.
Redman, J., Armstrong, S., and Ng, K. T., "Free-Running Activity Rhythms in the Rat: Entrainment by Melatonin", *Science*, vol. 219, pp. 1089–1091, 4 Mar. 1983.
Cramer, H., et al., "On the Effects of Melatonin on Sleep and Behavior in Man", *Advances in Biochemical Psychopharmacology*, vol. 11, pp. 187–191, 1974.
Carman, J. S., et al., "Negative Effects of Melatonin on Depression", *Am. J. Psychiatry*, 133:10, pp. 1181–1186, Oct. 1976.
Vollrath, L., et al., "Sleep Induction by Intranasal Application of Melatonin", *Advances in Bioscience*, 29, pp. 327–329, 1981.
Norlund, J. J., and Lerner, A. B., "The Effects of Oral Melatonin on Skin Color and on the Release of Pituitary Hormones", *JCE & M*, vol. 45, No. 4, pp. 768–774, 1977.
Anton-Tay, F. et al., "On the Effect of Melatonin Upon Human Brain. Its Possible Therapeutic Implications", *Life Sciences*, vol. 10, Part I, pp. 841–850, 1971.
Fevre-Montange et al., J. Clin. Endocrinol. Metab. 52 642–649 (1981).
Akerstedt et al., Biological Psychiatry 17 547–554 (1982).
Cramer et al., 1st. Europ. Congr. Sleep Res. Based 1972, pp. 488–491.
Reinhard et al., 2nd Europe. Congr. Sleep Res., Rome 1974, pp. 518–222.
Pavel et al., Adv. Biosciences 29 343–374(1981).
Chem. Abst. 94 (1981) 171,981 R.
Chem. Abst. 97 (1982) 33783 D.
Chem. Abst. 81 (1974) 86396R and 84(1976), 54600Y and 94(1981) 171799n.

*Primary Examiner*—Stanley J. Friedman
*Attorney, Agent, or Firm*—Larson and Taylor

[57] ABSTRACT

Disturbances in circadian rhythms of bodily performance and function, as may occur for example in transfer of work patterns from day to night-shift, or rapid crossing of several time zones in an aircraft ("jet lag") are treated by administration of melatonin. Alleviation or prevention of ill effects associated with disturbance of circadian rhythms is achieved by administration of melatonin in specified ways which are varied to suit particular needs and circumstances.

13 Claims, 4 Drawing Figures

METHOD FOR MINIMIZING DISTURBANCES IN CIRCADIAN RHYTHMS OF BODILY PERFORMANCE AND FUNCTION

This invention relates to a method of minimizing disturbances in function and performance rhythms in humans with disturbed circadian rhythms.

All forms of life, from plants, insects, amphibians, reptiles, birds and mammals, including humans, show cyclical patterns of activity of approximately 24 hours periodicity.

Circadian rhythms in bodily functions are defined as those events with a periodicity of about 24 hours which persist in the absence of external environmental cues. When a rhythm persists in the absence of external environmental cues it is said to be free-running. In man, the periodicity of these free-running rhythms is almost invariably greater than 24 hours. In normal life, these rhythms are reset (entrained) every day to about 24 hours by external environmental stimuli (zeitgebers), the light-dark cycle being of overriding importance.

A host of mammalian circadian rhythms have been described, including feeding, drinking, sleep-wake, rapid eye movement (REM) sleep, body temperature, physical and mental performance, cardiovascular activity, urine flow, electrolyte excretion and mitotic activity.

There are also pronounced daily rhythms in blood hormone concentrates of cortisol, noradrenaline, adrenaline, insulin, growth hormone, adrenocorticotrophic hormone, prolactin, luteinising hormone, testosterone, melatonin, arginine vasotocin, etc. etc.

In humans, it has been conclusively demonstrated that many of these rhythms free-run, e.g. sleep-wake, REM sleep, body temperature, cortisol, adrenaline, noradrenaline and melatonin and are therefore true circadian rhythms.

Experimentally it has been shown in humans that rhythms normally synchronized with each other in the presence of external environmental cues can free-run with different periodicities in the absence of external environmental cues. This is referred to as 'internal desynchronization'. For example, in the absence of environmental cues an individual might have a body temperature rhythm of 25 hours and a sleep-wake rhythm of 33 hours. On re-introducing an appropriate environmental cue these rhythms would become re-synchronized.

The phenomenon of internal desynchronization has been taken as evidence that there must be more than one central time clock or oscillator, and that in normal life these oscillators are kept in synchrony with one another by the entraining environmental stimuli. One would expect persons not experiencing the normal light-dark cycle, for example astronauts, submariners and polar explorers and certain blind individuals to suffer from internal desynchronization through not receiving the normal zeitgeber from the light-dark cycle.

The way in which photoperiod acts as an entraining stimulus for circadian rhythms is highly complex and still not completely understood. It is thought that separate neural oscillators are responsive to the daylight changes at dawn and dusk respectively, and that acting in concert these are responsible for the daily entrainment of the circadian rhythms. Thus these rhythms readily adapt to the gradual changes in the light-dark ratio with the progression of the seasons. Recent research suggests that the suprachiasmatic nuclei of the hypothalamus contain the dawn and dusk oscillators which play an integral role in the synchronization of circadian rythms.

A person subjected to a rapid alteration in the timing of day and night will find his body rhythms to be out of synchrony with the new environment, as in the case of somebody who starts to work on night shift, or who rapidly crosses several time zones in an aircraft. It may take a week or so for the various rhythms all to become reentrained, some responding faster than others. This transitory desynchronization is termed 'internal dissociation' and causes the symptoms of "jet lag", e.g. feeling sleepy and tired at times of day inappropriate to the sleep-work schedule of the new location or roster, with disturbed rhythms of appetite, urination, body temperature and performance of physical and mental tasks.

Reference is made to the following publications which have documented some effects experienced by humans subjected to abrupt time changes.

1. *Effects of flying and of time changes on menstrual cycle length and on performance of airline stewardesses.* Preston, F. S., Bateman, S. C., Short, R. V. and Wilkinson, R. (1973) Aerospace Medicine 44, 438–443.
2. *Effects of "Jet Lag" on Hormonal Patterns. I. Procedures, variations in total plasma proteins, and disruption of adrenocorticotropin-cortisol periodicity.* Desir, D., VanCauter, E., Fang, V. S., Martino, E., Jadot, C., Spire, J. P., Noel, P., Refetoff, S., Copinschi, G., Goldstein, J., 1981 J. Clin. Endocrinol Metab. 52:628.
3. *Effects of "Jet Lag" on Hormonal Patterns. II. Adaption of Melatonin Circadian Periodicity.* Fevre-Montange, M., VanCauter, E., Refetoff, S., Desir, D., Tourniaire, J., Copinschi, G., 1981 J. Clin Endocrinol Metab. 52:642.

It is a common experience of airline travellers that flights in a westerly direction (phase delay) are less stressful than flights in an easterly direction (phase advance). This may be because in the latter case some rhythms may phase-advance and some may phase-delay, thereby accentuating the degree of internal dissociation. Circadian biologists refer to this as entrainment by partition.

It has also been demonstrated that shift workers adapt to phase delays (analagous to westerly flights) better than to phase advances. This is presumably explained by the fact that the free-running rhythms are longer than 24 hours and these have a propensity to delay.

"Jet lag" is considered to be a symptom of internal dissociation.

The recent study by Desir et al (reference (2.) above) has confirmed that internal dissociation is associated with trans-meridian travel. Those researchers have also documented discernible differences between the effects of flights in a westerly direction and flights in an easterly direction (also see Fevre-Montange et al, reference (3.) above).

In contrast to the "jet lag" symptoms experienced by those individuals suffering from short-term internal dissociation as a results of a trans-meridian flight or an altered work roster, individuals with long-term internal desynchronization do not suffer in the same way. Astronauts, submariners, polar explorers and some blind people are likely to fall into this latter category since they are deprived of the normal photoperiodic entraining stimulus, and there is anecdotal evidence to suggest that some of them may have difficulty in synchronizing their sleep-wake times with the imposed work roster.

Volumes have been written on the subject of attempts to prevent or treat "jet lag" within the past decade in the scientific, medical and lay press, and the topic has been exhaustively reviewed.

TABLE 1
SUGGESTIONS IN THE LITERATURE FOR MINIMIZING "JET LAG"

GENERAL
1. Implementation of a travel-time formula which takes into account arrival and departure times and number of time-zones crossed.

PRE-FLIGHT ADAPTATION
1. Simulation of destination clock time.
2. Simulation of destination day-night cycle.
3. Simulation of destination life events eg. meal timing, going to bed and getting-up.

} Several days prior to departure.

FLIGHT ADAPTATION
1. Avoid alcohol.
2. Avoid heavy meals.
3. Do some exercise.

POST-FLIGHT ADAPTATION
1. Keep clock-time the same as that of country of origin.
2. Keep light-dark cycle the same as that of country of origin.
3. Build special hotels with facilities for keeping country of origin light-dark schedules and meal times, (as has been the practice of Russian air crews flying between the U.S.S.R. and Great Britain).
4. Schedule important meetings at times of day chosen on basis of country of origin time rather than destination time.
5. Arrive at destination several days in advance of important meetings.
6. Avoid isolation and maximize social interaction to promote synchronization.
7. Induce sleep by moderate exercise, eg. walking.
8. Induce sleep by taking a warm bath.
9. Induce sleep by taking hypnotics.
10. Avoid hypnotics.
11. Avoid alcohol.
12. Avoid tranquilizers.

} due to interference with REM sleep.

13. Manipulate meal timing.
14. Manipulate calorific content.
15. Avoid staying indoors and maximize exposure to daylight after arrival.

For further popular discussion of suggested methods to prevent and overcome jet lag see: "The Jet-lag Book" Kowet D, Crown Publishers Inc. and "Overcoming Jet lag" Ehret C. Berkley Books.

There is a growing list of substances known to influence (but not entrain) mammalian circadian rhythms. These include heavy water ($D_2O$), lithium, and the monoamine oxidase inhibitors, clorgyline and imipramine. Chronic administration of these compounds to laboratory animals lengthens the unentrained, free-running period, and the monoamine oxidase inhibitors split the rhythm.

As none of these substances actually entrain circadian rhythms none of these substances would be appropriate for treating "jet lag".

It has also been claimed that oestrogen, progesterone, testosterone and thyroxine, or their removal by gonadectomy or thyroidectomy, may influence the free-running period in laboratory animals. It has been suggested that in birds the daily rhythm in corticosteroid secretion could function as a master oscillator to entrain other circadian rhythms. Recently Alberto Angeli (Glucocorticoid Secretion: A Circadian Synchronizer of The Human Temporal Structure, 1983, J. Steroid Biochem, Vol. 19, No. 1, pp 545-554) has proposed such a mechanism for man. Since the corticosteroid rhythm is one of the last to reentrain following a time-zone change, it is difficult to see how this would operate.

Hypnotics and tranquillizers, e.g. diazepam, temazepam, oxazepam, triazolam, botizolam, are frequently used by the travelling public, and although they may induce sleep, its quality is in question since REM sleep is adversely affected. Some have even gone so far as to advise against the use of hypnotics because of their cumulative effects if taken repeatedly.

There is no scientific evidence to suggest that any of these compounds hastens the reentrainment of circadian rhythms.

A fundamental problem of the prior art has been the total lack of understanding of the phenomenon known as jet lag. Not surprisingly amidst the welter of contradictory claims there is little consensus.

Indeed there is little reason for the approach of workers in the prior art to have consensus for it was asserted by Aschoff, one of the pioneers of circadian biology, that the central nervous mechanisms that generate circadian rhythms must be chemically and thermally independent in order to ensure the precision of the body's timing mechanisms. Thus the system is rendered immune from unintentional manipulation by everyday extraneous influences. The approach of workers in the prior art has been to manipulate just one aspect of a particular circadian rhythm.

In the article "PHYSIOLOGICAL CHANGES UNDERLYING JET LAG" (British Medical Journal, Vol. 284, Jan. 16, 1982, pp 144-146), Arendt and Marks state at page 146:

"Anticipation of jet lag and its prevention by planned manipulation of circadian rhythmicity before departure is possible using particular food-intake protocols, but for most people such an approach is impracticable. Pharmacological manipulation of circadian rhythms poses even greater problems. Compounds including oestradiol, testosterone, theophylline, lithium, and tricyclic anti-depressants affect the length of the period of circadian rhythms in animals, but there have been few, if any, studies of their effects on human rhythms. Temporary discomfort is surely preferable to such medication. Recommendations for passengers by the Advisory Group for Aero Space Research and Development include the use of short-acting hypnotics during Transmeridional flights to lessen the effects of jet lag. Subsequently, an extended night's sleep, together with exposure to local social cues, is essential for rapid resynchronization. Aircrew were recommended to keep sleep deficit to a minimum, remain on home-base time, and return rapidly to base. The practical application of such recommendations clearly presents difficulties, with particular reference to remaining on home-base time. Various formulae have been devised for calculating the rest-time necessary to achieve resynchronization, depending on the number of time-zones crossed, flight duration, times of departure and arrival, and direction of flight, as well as the individual's age." (emphasis added)

Clearly these reviewers consider the prior art to be teaching away from the use of pharmacological manipulation of circadian rhythms in order to relieve the symptoms of "jet lag".

Melatonin is another hormone with a pronounced 24 hour rhythm, the levels being elevated during the night time in all species. It is secreted by the pineal gland, but pinealectomy in rats is without effect on their free-running circadian rhythms, suggesting that in mammals melatonin is not involved in the generation of such rhythms.

Pinealectomy of rats and hamsters accelerates reentrainment after a phase shift in the light-dark cycle. Thus if the removal of melatonin speeds up the readjustment following a phase shift, melatonin administration would be expected to have the opposite effect and postpone reentrainment. From these findings one would expect melatonin to be contraindicated for a person suffering from jet lag.

The first demonstration of chemical entrainment in mammals was published by Redman, J., Armstrong, S., and Ng, K. T., in Science, 1983 Vol. 219, pp 1089–1091. Contrary to the above predictions, they showed that pharmacological doses of melatonin could entrain the free-running circadian activity rhythm of rats, but only when melatonin was given at the time of onset of spontaneous activity. But since endogenous melatonin levels in rats are elevated at the time of maximal activity whereas in humans they are elevated during sleep, the connection between the rat results and the problem of jet lag in humans is not apparent.

A chronobiotic is defined for present purposes as a substance which is capable of therapeutically reentraining short-term dissociated or long-term desynchronized circadian rhythms, or prophylactically preventing their disruption following an environmental insult. The surprising discovery of the present invention is that melatonin is a powerful chronobiotic in humans. This discovery is contrary to all expectations. Melatonin is released by the pineal gland in a rhythm generated by the suprachiasmatic nuclei. It was therefore highly surprising to discover that melatonin produced by the "slave" organ was capable of feeding back to regulate some functions of the "master" oscillator, the suprachiasmatic nuclei.

The role played by the suprachiasmatic nuclei in regulating the release of melatonin by the pineal has been reviewed by Winfree (CIRCADIAN TIMING OF SLEEPINESS IN MAN AND WOMAN, Winfree A. T., American Journal of Physiology, Vol. 243, 1982, pp 193–204).

It has been long known that pharmacological doses of melatonin administered to human subjects induces drowsiness and sleep as do other hormones like progesterone. (See: ON THE EFFECTS OF MELATONIN ON SLEEP AND BEHAVIOUR IN MAN, Cramer H, Rudolph J, Consbruch V, Kendel K. 1974, Advances in Biochemical Psychopharmacology, Vol. 11, pp 187–191 Raven Press, NY). The architecture of this melatonin-induced sleep is more natural than that produced by currently available sleeping pills, which suppress REM sleep. However, this cannot be taken as evidence that melatonin is the physiological compound normally responsible for sleep; one can fall asleep during the daytime when melatonin levels are at their lowest, and melatonin levels can be dissociated from the sleep pattern for several days following an abrupt time-zone change. This is perfectly in keeping with the observation that hypnotics can induce sleep but do not reentrain circadian rhythms. The well documented hypnotic role of melatonin has not previously been linked with reentrainment of circadian rhythms.

Within the last 10 years it has been shown that physiological doses of melatonin administered by mouth, by implant or by injection are capable of altering the timing of the annual breeding season in hamsters, sheep, ferrets and deer, and the present inventors have demonstrated similar effects in wallabies. A review of these potential commercial applications of melatonin appeared in Nature on Apr. 28th, 1983 (Vol. 302 p 755), and it is interesting that no mention was made of the possibility that melatonin might regulate events such as "jet lag".

Notwithstanding such work, in 1983 Arendt hypothesised (with no experimental evidence to support her contention) that melatonin might be able to shift circadian rhythms in man and reorganize the circadian system when it is pathologically disturbed. (BIOLOGICAL RHYTHMS Arendt J., International Medicine, Vol. 3, Number 2, 1983 pp 6–9). However that researcher did not identify "jet lag" as internal dissociation nor did she establish that melatonin would in fact shift circadian rhythms. Arendt did not specify or suggest a pharmacological procedure involving melatonin that might achieve the hypothesised response.

It is clear from our results that exogenous melatonin can act as a chronobiotic in man since it can hasten the reentrainment of the body temperature rhythm following an abrupt time-zone change or a change in work roster such as that experienced by night-shift workers. It is well known from some of our own and other earlier work that performance in cognitive tasks is closely linked to the body temperature rhythm (see: Colquhoun, W. P., Biological rhythms and human performance, Academic Press, 1971), and that the duration and organization of human sleep is dependent on the circadian phase of the body temperature rhythm (Czeisler, C. A., Weitzman, E. D., Moore-Ede, M. C., Zimmerman, J. C., Knaver, R. S.; 1980 SCIENCE, Vol. 210, pp 1264–1267). We therefore believe that the beneficial effects of melatonin in our experiments are due to its ability to hasten the reentrainment of body temperature rhythms, from which many other rhythms flow. Individuals such as astronauts, submariners, polar explorers or blind people, would benefit from timed daily administration of melatonin.

There is an interesting relationship between time zone changes and psychiatric illness. Depressive illnesses are higher in incidence after a westward flight while mania is higher after an eastward flight. Since a westward flight is a phase delay of the zeitgeber this leaves, at least initially, the sleep span advanced relative to the new night-time. This fits in exactly with the phase-advanced hypothesis of depression. This states that in endogenous depression, various circadian rhythms are shifted abnormally early (phase advanced) relative to the night-day cycle (Antidepressants and a circadian rhythm phase-advance hypothesis of depression, by T. A. Wher et al, pp 263–274 in Brain Neurottansmitters and Hormones edited by R. Collu et al, Raven Press, 1982). Therefore, melatonin administered at the appropriate time of day could be used in treatment of all psychotic illnesses which result from abnormal timing of circadian rhythms. The only study in which melatonin has been administered to depressed patients reported an exacerbation of symptoms including florid psychotic episodes (CARMAN, J. S. et al AMERICAN JOURNAL OF PSYCHIATRY 133, pp 1181-1186, 1976).

The prior art is teaching away from the use of melatonin to relieve psychoses, since researchers have made no allowance in the experimental procedures for the time of day of administration of melatonin and melatonin's capacity to re-entrain circadian rhythms in humans.

The object of this invention is to minimize the disturbances in human bodily performance and function that occurs in the absence of an appropriate photoperiodic zeitgeber or time cue.

By the method of the present invention administration of the hormone melatonin is used as a zeitgeber to rapidly entrain certain circadian rhythms to a new photoperiodic environment, thereby minimizing the period of disturbance consequent upon the disruption of these rhythms.

It is known that the pineal gland secretes its principal hormone, melatonin (5-methoxy-N-acetyltryptamine) according to a circadian rhythm generated in the suprachiasmatic nuclei of the hypothalamus and entrained by photoperiod. The pineal gland acts as a neuro-endocrine transducer, converting a neural input, in the form of light acting on the retina, into an endocrine output, in the form of melatonin which is released into the systemic circulation to act back on the brain directly. The pineal gland may also release other regulatory compounds such as arginine vasotocin which act back on the brain.

Since the circadian rhythm of melatonin secretion from the pineal is governed by a circadian rhythm generated in the suprachiasmatic nuclei and is entrained by light, our invention is surprising as we are using the product of this rhythm, melatonin to act back on the rhythm-generating mechanism within the suprachiasmatic nuclei to reentrain them. Our understanding of feedback systems would predict that exogenous administration of melatonin would be ineffective since it would merely suppress endogenous release. The surprising discovery is that by applying the method of the present invention reentrainment is hastened.

It is known from measurements of melatonin in blood and of its metabolites in urine that in all species investigated, including the human, melatonin is produced predominantly if not exclusively at night. It has also been observed that this nocturnal secretory pattern takes several days to readjust to a sudden time change.

Application of the method should normally commence immediately following a time change, when the person would be trying to go to sleep according to the new time schedule. By raising the amount of melatonin in the circulation this will not only induce a sense of drowsiness, helping the person to go to sleep, but it will also improve the quality of the sleep and entrain the circadian rhythms to the new imposed photoperiod. While the invention has been described with reference to the administration of melatonin, other related indoles or indole derivates may be used. It has been shown that synthetic melatonin analogs do express varying degrees of melatonin agonist activity when tested on fish bioassay (STRUCTURE-ACTIVITY RELATIONSHIP OF MELATONIN ANALOGUES Frohn M. A., Seaborn C. J., Johnson D. W., Phillipou G., Seamark R. F., Matthews C. D., Life Science Vol. 27, pp 2043-20456, 1980).

Treatment in accordance with the invention may be used by a person until all their bodily rhythms have adjusted to the new environment. It may also be possible to use the treatment to adjust the circadian rhythms in advance of a time change, thereby anticipating the new environment.

The preferred schedule for treatment requires the subject to take a specified preparation of melatonin at the anticipated time for going to sleep in the new destination or a new activity schedule. The treatment should be taken at least at the commencement of the first sleep period of the new destination. Alternatively treatment may be commenced 1 or more days prior to the commencement of the journey or during the journey at the time anticipated to be the commencement of sleep time in the new time zone.

The method of the invention may be achieved by the oral administration of exogenous melatonin, the preferred dosage range being from 1-10 mg.

The timing of the melatonin administration and the period of time for which the blood level remains elevated are important parameters for control when performing the method of the invention. Any pharmaceutical preparation containing melatonin in a pharmacologically effective concentration would be suitable for performing the method of the invention. Maintaining high plasma levels of melatonin throughout the desired sleep period is preferable. Alternatively, it may be necessary to take additional melatonin if the person wakes during the desired sleep period.

While people have administered melatonin before it is not part of the prior art to formulate a dose of melatonin into a slow release form. Our research has shown that it is preferable to maintain appropriate plasma levels of melatonin during the entrainment procedure. Clearly melatonin in a slow release form enables the desired plasma levels to be maintained without the need to take further doses during a particular sleep period.

While oral administration is the preferred route of administration of melatonin any other route may be used to achieve the desired plasma levels in accordance with the method of the invention.

In view of the known effects of high intensity light in inhibiting endogenous melatonin release in man (A. LEWY et al Science, Vol. 210 : pp 1267-1268, 1980) it would be advisable to make use of the phenomenon to bleach out the old endogenous melatonin rhythm following a time zone or work roster change, whilst taking exogenous melatonin to stimulate the development of the new melatonin rhythm. It is also known that beta blockers such as PROPANOLOL can inhibit endogenous melatonin secretion so these could also be used to eliminate the old endogenous melatonin rhythm following a time zone or work roster change.

It is known that the enzyme N-acetyl transferase which converts serotonin to N-acetylserotonin provides a rate limiting step in the production of melatonin by the pineal gland. Therefore the method of the invention may also be achieved by administering N-acetylserotonin or any of its intermediates in the synthesis of melatonin as the therapeutic agent. Since exogenous L-dopa administration stimulates melatonin synthesis, and presumably release in rats, this method of increasing melatonin bioavailability at an appropriate time of the day is also useful for performing the method of the present invention.

The invention may also include a package containing melatonin in appropriate dosage form, said package including instructions for administration thereof, consistent with the teachings herein for the alleviation or prevention of ill effects associated with disturbance of circadian rhythms.

EXAMPLE 1

Figure 1:
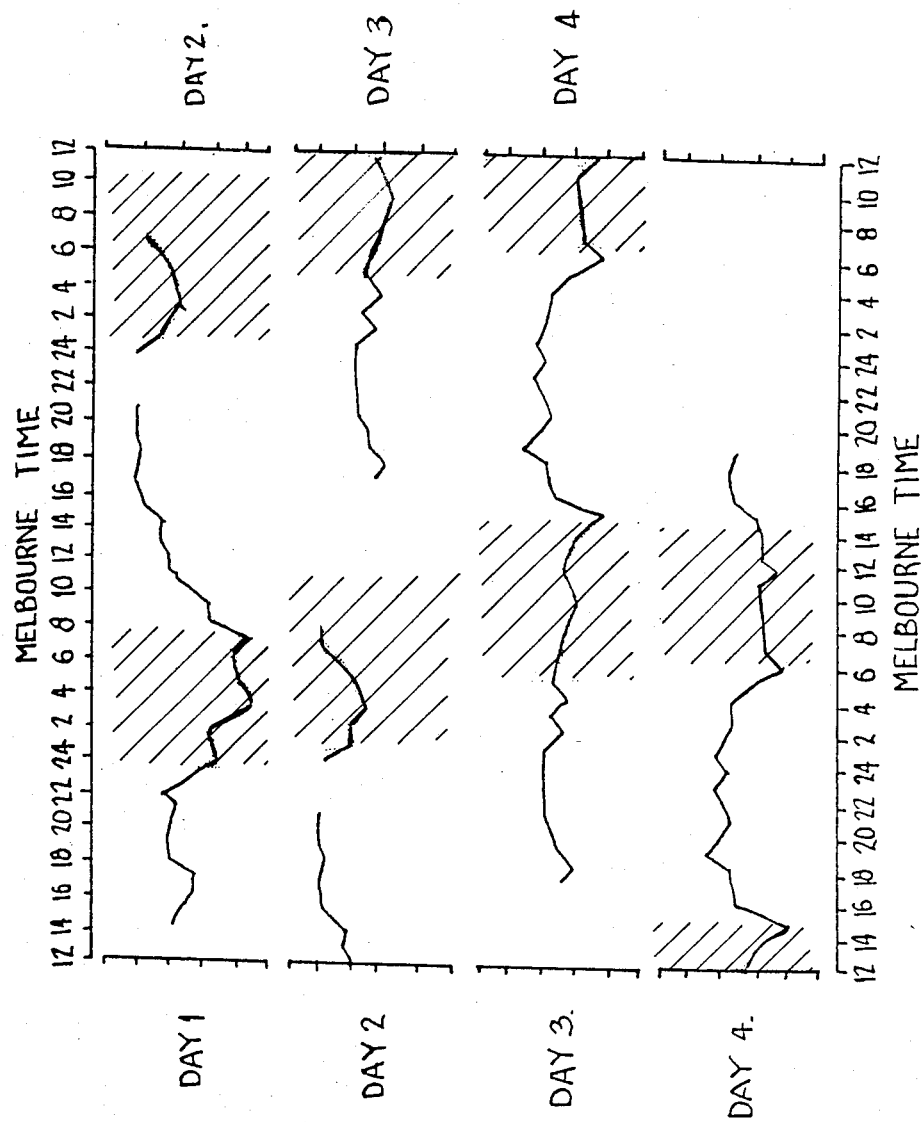
FIGS. 1, 3 and 4 are graphical temperature records of subjects treated in accordance with the invention.

This example demonstrates the effectiveness of the present invention at alleviating the distressing effects on circadian rhythms during a west out, east back flight through several time zones.

Subject A was a Professor of Physiology who had never taken melatonin before.

been tired, inattentive, unable to concentrate, and felt totally disoriented in time.

On the return flight, Subject A put himself back on Melbourne time and took melatonin in Hawaii to enable him to sleep Melbourne time. As a result, he arrived back in Melbourne in the afternoon feeling fine, and slipped easily into his normal Melbourne routine, going to bed at 11.30 p.m. and sleeping normally to awake at the usual time of 8.00 a.m. Subject A slept normally for the following three nights, and never felt any fatigue whatsoever from a rather punishing schedule.

Subject A's rapid return to normality on his return to Melbourne probably reflects the fact that the 3 days in the U.S.A. had been insufficient to disturb all of his circadian rhythms, which remained essentially on Melbourne time throughout the trip. However, the melatonin treatment in the U.S.A. certainly seemed to entrain his sleep-wake and performance rhythms to U.S.A. time.

| Flight from Melbourne → North Carolina, U.S.A. → Melbourne. 16.4.83-20.4.83 Details of activity schedule, sleeping time, melatonin administration. | | |
|---|---|---|
| Melbourne Time | Activity and Location | Local Time |
| 1205 hrs 16.4.83 | Left Melbourne by air | |
| 1315 hrs 17.4.83 | Arrived Chapel Hill, North Carolina. | 2215 hrs 16.4.83 |
| 1400 hrs | To bed, took 2.5 mg Melatonin, fell asleep ↓ | 2300 hrs |
| 1730 hrs | Awoke spontaneously, took 5.0 mg Melatonin, fell asleep again ↓ | 0230 hrs 17.4.83 |
| 0030 hrs 18.4.83 | Awoke spontaneously Felt fresh, relaxed, not jet-lagged ↓ Worked a normal day, chairing Board Meetings ↓ | 0930 hrs |
| 1330 hrs | To bed, took 5 mg Melatonin, fell asleep ↓ | 2230 hrs |
| 1615 hrs | Awoke spontaneously took 5.0 mg Melatonin, fell asleep again ↓ | 0115 hrs 18.4.83 |
| 1815 hrs | Awoke spontaneously, took 5.0 mg Melatonin, fell asleep again. ↓ | 0315 hrs |
| 2245 hrs | Awoke spontaneously, felt fresh, relaxed. ↓ Worked a normal morning. In afternoon, caught flight back to | 0745 hrs. |
| 0875 hrs 19.4.83 | Melbourne, departing at ↓ | 1657 hrs. |
| 2315 hrs | Hawaii. Took 2.5 mg Melatonin. Fell asleep. ↓ | 0315 hrs 19.4.83 |
| 0600 hrs 20.4.83 | Awoke spontaneously, feeling fresh. ↓ Worked on plane | |
| 1515 hrs | Arrived Melbourne Airport ↓ | |
| 2330 hrs | To bed no Melatonin ↓ | |
| 0800 hrs | Awoke normally. | |

COMMENT

Although subject A awoke once or twice during the night in North Carolina, he fell asleep again within 15 minutes of taking additional melatonin on each occasion.

Subject A awoke spontaneously each morning in the U.S.A. feeling in top form, and was able to carry out a heavy work schedule during the day with no symptoms of jet lag whatsoever.

Following a similar itinerary, on previous occasions, without taking melatonin Subject A had consistently This example demonstrates that the method of the present invention is capable of altering a human's circadian rhythms to avoid the distress associated with a rapid transition from one time zone through at least a second time zone and then return to the first time zone. The most remarkable positive effect in this instance was that Subject A could alter his sleep routine and work routine to suit each time zone visited.

In this example Subject A used a preparation of crystalline melatonin in a gelatine capsule.

EXAMPLE 2

| | Flight from Melbourne → Munster, W. Germany → Melbourne. 27.5.83–5.6.83 Details of activity schedule, sleeping time, melatonin administration. | |
|---|---|---|
| Melbourne Time | Activity and Location | Local Time |
| 1540 hrs 27.5.83 | Left Melbourne by air | |
| 0140 hrs 29.5.83 | Arrived Munster, W. Germany | 1740 hrs 28.5.83 |
| 0700 hrs | To bed, took 5 mg Melatonin | 2300 hrs |
| 1550 hrs | Awoke spontaneously | 0750 hrs |
| | Felt fresh and rested, much less tired. | 29.5.83 |
| | Worked a normal day, scientific meetings | |
| 0635 hrs 30.5.83 | To bed, took 5 mg Melatonin | 2235 hrs |
| 1120 hrs | Awoke spontaneously, took 5 mg Melatonin fell asleep. | 0320 hrs 30.5.83 |
| 1415 hrs | Awoke spontaneously, feeling excellent | 0615 hrs |
| | Worked a normal day, scientific meetings | |
| 0840 hrs 31.5.83 | To bed, took 5 mg Melatonin | 0040 hrs 31.5.83 |
| 1205 hrs | Awoke spontaneously, took 5 mg Melatonin, fell asleep. | 0405 hrs |
| 1505 hrs | Awoke spontaneously, feeling fine | 0705 hrs |
| | Worked a normal day, scientific meetings | |
| 0926 hrs 1.6.83 | To bed, took 5 mg Melatonin | 0125 hrs 1.6.83 |
| 1030 hrs | Awoke spontaneously, but fell asleep again with no additional Melatonin | 0230 hrs |
| 1400 hrs | Awoke spontaneously feeling good. | 0600 hrs |
| | Flew to Frankfurt, drove to Munich | |
| 0545 hrs 2.6.83 | To bed, headache, feeling tired. No Melatonin. Fell asleep at once. | 2145 hrs |
| 1445 hrs | Awoke spontaneously, feeling fine | 0645 hrs 2.6.83 |
| | Scientific meetings, flew to Frankfurt. | |
| 0720 hrs 3.6.83 | To bed, no Melatonin, fell asleep at once | 2320 hrs. |
| 1430 hrs | Awoke spontaneously, feeling very fresh. | 0630 hrs 3.6.83 |
| 0550 hrs 4.6.83 | Caught flight to Melbourne, departing at | 2150 hrs |
| 0835 hrs | Slept from Rome to Bombay, going to sleep at Rome time. | 0035 hrs 4.6.83 |
| 1400 hrs | Awoke spontaneously, feeling O.K. | |
| 0000 hrs (midnight) | Took 5 mg Melatonin, slept deeply. | |
| 0610 hrs 5.6.83 | Awoken by breakfast, felt fresh and rested. | |
| 0700 hrs | Landed Melbourne | |
| | Spent day gardening | |
| 2100 hrs | To bed, took 5 mg Melatonin | |
| 0810 hrs 6.6.83 | Awoke spontaneously after good sleep. Felt tired during the day. | |
| 2315 hrs | To bed, took 5 mg Melatonin, slept very well. | |
| 0745 hrs 7.6.83 | Awoke spontaneously, felt excellent, busy day in laboratory. | |
| 2245 hrs | To bed, took 5 mg Melatonin, slept well. | |
| 0745 hrs 8.6.83 | Awoke spontaneously with a slight hangover. | |

| Flight from Melbourne → Munster, W. Germany → Melbourne. |
| --- |
| 27.5.83–5.6.83 |
| Details of activity schedule, sleeping time, melatonin administration. |

| Melbourne Time | Activity and Location | Local Time |
| --- | --- | --- |
| | Discontinued medication. | |

COMMENT

The melatonin allowed Subject A to sleep well following both Westerly and Easterly flights with an 8-hour time zone change. Subject A awoke spontaneously each morning at the appropriate (local) time feeling excellent, and experienced no symptoms of jet lag apart from tiredness on the second day after his return to Melbourne.

This example demonstrates that with the method of the present invention it is possible to rapidly entrain sleep routines to suit an interary that crosses several time zones over a period of a week.

As in Example 1, Subject A took melatonin packaged in a gelatine capsule.

In both examples, Subject A spontaneously awoke during entrainment sleep. Upon taking another capsule he returned to sleep. These experiments show that the preferred way of performing entrainment would be with melatonin made up in a long-acting preparation.

EXAMPLE 3

| Subject A Flight from Melbourne → Stockholm → London → Melbourne. |
| --- |
| 25.6.83–11.7.83. |
| Detail of activity schedule, sleeping times, melatonin administration. |

| Melbourne Time | Activity and Location | Local Time |
| --- | --- | --- |
| 1300 hrs 25.6.83 | Left Melbourne by air. | |
| 2100 hrs 26.6.83 | Arrived Stockholm, took bus to Uppsala. | 1300 hrs 26.6.83. |
| 0715 hrs 27.6.83 | To bed, took 5 mg Melatonin | 2315 hrs |
| 1222 hrs | Awoke spontaneously, took 5 mg Melatonin, fell asleep again. | 0422 hrs 27.6.83. |
| 1435 hrs | Awoke spontaneously, feeling fine ↓ Attended Acta Congress in Stockholm, evening reception and party. Felt good. ↓ | 0635 hrs |
| 1207 hrs 28.6.83 | To bed, took 5 mg Melatonin ↓ | 0407 hrs 28.6.83 |
| 1700 hrs | Awoke spontaneously. Felt good. Attended Congress and reception and evening party. ↓ | 0800 hrs |
| 1208 hrs 29.6.83 | To bed, took 5 mg Melatonin ↓ | 0408 hrs 29.6.83. |
| 1630 hrs | Awoke spontaneously feeling good. Attended Acta Congress, boat trip in evening. ↓ | 0830 hrs |
| 0945 hrs 30.6.83 | To bed, took 5 mg Melatonin ↓ | 0145 hrs 30.6.83 |
| 1540 hrs | Awoke spontaneously, feeling fine. ↓ Acta Congress all day ↓ | 0740 hrs |
| 1152 hrs 1.7.83 | To bed, did not take any Melatonin ↓ | 0352 hrs 1.7.83 |
| 1600 hrs | Awoke spontaneously feeling fine ↓ Flew to London and train to Cambridge - stayed one night; Bristol - stayed 4 nights; London, stayed one night. No problems sleeping, waking or with feelings of well being. No records kept until return flight starting on 9.7.83. | 0800 hrs |
| 0630 hrs 10.7.83 | Left London by air. Feeling very tired after a hot day, so slept on plane. | 2130 9.7.83 |
| 1445 hrs | Awoke spontaneously. | |
| 1700–1900 hrs | Slept. | |
| 2130 | Flight arrived Singapore | 1930 hrs (1230 hrs London time) |
| 2345 hrs | Took 5 mg Melatonin, fell asleep ¾ hour later. | 2145 hrs (1445 hrs London time) |
| 0500 hrs 11.7.83 | Awoken by breakfast after a good sleep, but could have slept longer. | |
| 0947 hrs | Arrived Melbourne Airport. Went home, shower, shave, went in to lab. for 1 hour lecture and then discussions with Medical students. Felt fine. | |
| 2334 hrs | To bed, took 5 mg Melatonin, slept well. | |
| 0800 hrs 12.7.83 | Awoke to alarm. Feeling fine. Normal working day. Felt fine. | |

-continued

Subject A Flight from Melbourne → Stockholm → London → Melbourne.
25.6.83–11.7.83.
Detail of activity schedule, sleeping times, melatonin administration.

| Melbourne Time | Activity and Location | Local Time |
|---|---|---|
| 2247 hrs | To bed, took 5 mg Melatonin, did not go to sleep until 2330 hrs. | |
| 0800 hrs 13.7.83 | Awoke by alarm. Feeling fine. Normal working day. Felt fine. | |
| 2324 hrs | To bed, took 5 mg Melatonin, fell asleep 2400 hrs. | |
| 0745 hrs 14.7.83 | Awoke spontaneously, feeling fine. Normal working day. | |
| 2300 hrs | To bed, did not take Melatonin. | |
| 0800 hrs 15.7.83 | Awoke to alarm, feeling fine. Discontinued record. | |

COMMENT

Once again, the melatonin allowed Subject A to sleep well at an inappropriate time of the day following both Westerly and Easterly flights with an 8–9 hour time change. It was interesting that in Sweden he was quite sleep-deprived, going to bed in the early hours of the morning after much social activity and some alcohol at parties and receptions, nevertheless he always awoke at an appropriate local time feeling refreshed, and did not need to take additional melatonin at night.

Subject A also encountered no problems on his return to Melbourne, and was able to lecture to a class of 170 Medical students within 4 hours of stepping off the plane. At no time during the day either in Sweden or on his return to Melbourne did he feel jet-lagged.

The example demonstrated the ability of the method of the present invention to rapidly entrain circadian rhythms. Rapid entrainment to periods that vary every 24 hours is clearly demonstrated.

EXAMPLE 4

Subject A—Flight from
Melbourne→Geneva→London→Chapel Hill, North
Carolina→Melbourne 18.9.83–30.9.83

This example demonstrates the intimate relationship between the human body circadian rhythms of temperature and performance.

During this experiment use was made of a portable Vitalog PMS8 mini computer to record the temperature of Subject A. The Vitalog PMS8 recorded body temperature at ten minute intervals utilizing a rectal temperature probe. The temperature record has been displayed in FIG. 1. A discussion of the temperature record follows.

During this flight Subject A wore the Vitalog PMS8 mini computer and rectal probe for the continuous recording of his deep body temperature. The equipment malfunctioned after 4 days due to premature battery failure. From 18.9.83–23.9.83 Subject A kept a detailed daily log of quality and nature of sleep, mood, and alertness according to a technique developed by NASA.

Details of activity schedule, sleeping time, melatonin administration.

| Melbourne Time | Activity and Location | Local Time |
|---|---|---|
| 1300 hrs 18.9.83 | Left Melbourne by air. | |
| 1610 hrs 19.9.83 | Arrived Geneva | 0810 hrs 19.9.83 |
| | Spent morning walking round lake, committee meeting at WHO all afternoon. | |
| 0535 hrs 20.9.83 | To bed, took 5 mg Melatonin, fell asleep at once. | 2135 hrs |
| 1155 hrs | Awoke spontaneously, took 5 mg Melatonin, fell asleep after 30 min. | 0355 hrs 20.9.83. |
| 1500 hrs | Awoken by alarm, feeling excellent | 0700 hrs |
| | Worked all day at WHO. | |
| 0640 hrs 21.9.83 | To bed, took 5 mg Melatonin. | 2240 hrs |
| 1234 hrs | Awoke feeling drowsy, slight headache, took 5 mg Melatonin. Asleep 30 mins. | 0434 hrs 21.9.83 |
| 1500 hrs | Awoken by alarm, feeling fine. | 0700 hrs |
| | Worked all day at WHO. | |
| 0626 hrs 22.9.83 | To bed, took 5 mg Melatonin. Asleep 30 mins later. | 2226 hrs |
| 1145 hrs | Awoke spontaneously, took 5 mg Melatonin. | 0345 hrs |

-continued

| Melbourne Time | Activity and Location | Local Time |
|---|---|---|
| | Did not fall asleep, but lay in bed awake thinking of many research ideas. Eventually | 22.9.83 |
| 1400 hrs | fell asleep at | 0600 hrs |
| 1450 hrs | Awoken by alarm, feeling good. | 0650 hrs |
| | Worked all day at WHO. | |
| 0807 hrs 23.9.83 | To bed, took 5 mg Melatonin, fell asleep at once. | 0007 hrs 23.9.83 |
| 1430 hrs | Awoke spontaneously, feeling fine. | 0630 hrs |
| | Worked all day at WHO. | |
| 0240 hrs 24.9.83 | Left Geneva by air. | 1840 hrs |
| 0700 hrs | Arrived at hotel in London. | 2200 hrs |
| 0933 hrs | To bed, did not take Melatonin. | 0033 hrs 24.9.83 |
| 1530 hrs | Awoke spontaneously, felt fine. | 0630 hrs |
| 0130 hrs 25.9.83 | Left London by air | 1630 hrs |
| 1200 hrs | Arrived Raleigh/Durham, U.S.A. | 2200 hrs |
| 1335 hrs | To bed in Chapel Hill, took 5 mg Melatonin, fell asleep after 30 mins. | 2335 hrs |
| 1532 hrs | Awoke with proctalgia - took two codeine and disprin - fell asleep at once. | 0132 hrs 25.9.83 |
| 2050 hrs | Awoke spontaneously, felt fine. | 0650 hrs |
| | Worked all day at FHI chairing meetings. | |
| 1355 hrs 26.9.83 | To bed, took 5 mg Melatonin, fell asleep at once. | 2355 hrs |
| 2045 hrs | Awoke spontaneously feeling fine | 0645 hrs |
| | Worked all day at FHI, chaired meetings. | 26.9.83 |
| 1333 hrs 27.9.83 | To bed, took 5 mg Melatonin, fell asleep at once. | 2333 hrs |
| 2035 hrs | Awoke spontaneously, felt fine. | 0635 hrs |
| | Worked all day at FHI, gave seminar in morning. Flew in afternoon to Washington, D.C. | 27.9.83 |
| 1127 hrs 28.9.83 | To bed, took 5 mg Melatonin, asleep in half an hour. | 2127 hrs |
| 1615 hrs | Awoke, worried about catching early morning flight. Dozed fitfully for 2 hr 30 mins. | 0215 hrs 28.9.83 |
| 1851 hrs | Got up. Slight headache, so took 2 aspirins. | 0451 hrs |
| 2115 hrs | Flew from Washington National Airport to San Francisco via Minneapolis, clock back 3 hrs. Dozed 1 hr 30 mins on flight. | 0715 hrs |
| 0530 hrs 29.9.83 | Arrived San Francisco. | 1230 hrs |
| | Visit Dr Graeber and Dr Gander at NASA Aerospace Center, Manned Vehicle Systems Research Division, Ames. Changed computer battery. | |
| 1230 hrs | Departed San Francisco. | 1930 hrs. |
| 1400 hrs | Arrived Los Angeles, changed planes. | 2100 hrs |
| 1530 hrs | Flew to Sydney | 2230 hrs |
| 1800 hrs | Slept for 1 hr 30 mins until dinner at | 0100 hrs 29.9.83 |
| 1932 hrs | Took 5 mg Melatonin, asleep at once. | 0232 hrs |
| 2335 hrs | Awoke. Took 5 mg Melatonin, fell asleep at once. | 0635 hrs. |
| 0323 hrs 30.9.83 | Awoken by neighbour on plane. | |

| Melbourne Time | Activity and Location | Local Time |
| --- | --- | --- |
| | -continued | |
| 0632 hrs | Landed at Sydney. | |
| 0745 hrs | Took off for Melbourne | |
| 0909 hrs | Landed Melbourne | |
| | Stayed at home all day. In the evening, felt very tired and sleepy and cold. | |
| 2150 hrs | To bed, took 5 mg Melatonin, fell asleep in 25 mins. | |
| 0152 hrs 1.10.83 | Awoke to defaecate. Took 5 mg Melatonin. Fell asleep at once. | |
| 0800 hrs | Awoken by baby. Felt very sleepy, but this soon passed. | |
| 0815 hrs | Worked in garden all day. | |
| 2220 hrs | To bed, took 5 mg Melatonin, slept soundly. | |
| 0815 hrs 2.10.83 | Awoken by baby. Felt fine. | |
| | At home all day. | |
| 2212 hrs | To bed, took 5 mg Melatonin. Disturbed once in night by baby, but fell asleep again. | |
| 0730 hrs 3.10.83 | Awoke spontaneously. Felt fine. | |
| | Normal day at work. | |
| 2200 hrs | To bed, no Melatonin. Asleep by 2230 hrs. | |
| 0700 hrs 4.10.83 | Awoken by baby. | |
| | Normal day at work. | |
| 2330 hrs | To bed, asleep at once. | |
| 0600 hrs 5.10.83 | Awoke spontaneously. Record discontinued. | |

COMMENT

On this round-the-world flight in a Westerly direction Melatonin once again enabled Subject A to sleep when he wanted to, and to awake at a normal local time. Each morning Subject A felt fresh and relaxed, and was able to function during the ensuing days with no subjective symptoms of jet-lag.

FIG. 1 displays the temperature record of Subject A for four days.

The dark, dotted regions represent dark periods. The time scale is for Melbourne time no matter where Subject A actually was when the recording was made. Each dark period is identified by one of the letters A, B, C, D or E. Recordings of dark periods B, C and D have been repeated to give continuity to the record.

The black arrows identify the times of administration of melatonin.

The Vitalog rectal probe was inserted the day before departure at 1400 hrs on 17.9.83 and the accompanying graph shows the expected nocturnal fall during the first night of sleep (Dark Period A). The second sleep period occurred on the plane en route to Geneva, and again showed a nocturnal fall. The third and fourth sleep periods assisted by melatonin administration (black arrows) took place after arrival in Geneva, although the record is incomplete due to battery failure. The lowest temperatures were now occurring at around mid-day Melbourne time, coincident with the new sleep period, whilst maximal temperatures were occurring at around midnight Melbourne time. This shows that his body temperature rhythm had re-entrained extremely rapidly to Geneva time, under the influence of exogenous melatonin.

It is well known that performance rhythms are closely allied to the body temperature rhythm, performance being highest when body temperature is highest. The results of this experiment suggest that the melatonin prevented the subjective feelings of jet-lag by re-entraining Subject A's body temperature rhythm, and hence his performance, to the new time-zone. Without the method of the present invention, it would have taken Subject A's temperature rhythm several days to readjust to such a rapid and large time-zone change.

The temperature record has provided useful date on the temperature circadian rhythm and its response to entrainment by melatonin.

EXAMPLE 5

Subject B—Flight from
Melbourne→Geneva→Rotterdam→Melbourne 30.1.84–19.2.84

This was a double-blind trial. The subject, a Clinical Professor who had never taken Melatonin before, was given two bottles labelled A and B containing identical-looking gelatin capsules, and told to take one capsule A on goint to bed, and again if awaking in the middle of the night, for the first 4 days after arrival in Geneva. He was told to take one capsule B according to the same schedule after return to Melbourne, and to record the quality of each night's sleep and feelings during the daytime. Capsule A contained 5 mg Melatonin, and capsule B contained a placebo (sucrose). Only after the subject had completed his written report 4 days after returning to Melbourne was he told which pills contained Melatonin and which contained placebo.

| Details of activity schedule, sleeping time, melatonin administration. |||
| Melbourne Time | Activity and Location | Local Time |
| --- | --- | --- |
| 1345 hrs 30.1.84 | Left Melbourne by air | |
| 2130 hrs 31.1.84 | Arrived Geneva | 1130 hrs 31.1.84 |
| 0630 hrs 1.2.84 | To bed, took Capsule A, fell asleep | 2030 hrs |
| 1115 hrs | Awoke, took Capsule A, fell asleep again | 0115 hrs 1.2.84 |
| 1700 hrs | Awoken by alarm | 0700 hrs |
| | Worked all day at WHO, felt tired in afternoon | |
| 1315 hrs 2.2.84 | To bed, took Capsule A, fell asleep | 0315 hrs 2.2.84 |
| 1700 hrs | Awoken by alarm, having slept well | 0700 hrs |
| | Worked all day at WHO, felt tired in morning | |
| 0930 hrs 3.2.84 | To bed, took Capsule A, fell asleep | 2330 hrs |
| 1330 hrs | Awoke, took Capsule A, fell asleep again | 0330 hrs 3.2.84 |
| 1600 hrs | Awoke spontaneously having slept well | 0600 hrs |
| | Worked all day at WHO, felt tired in afternoon | |
| 1035 hrs 4.2.84 | To bed, took Capsule A, fell asleep | 0035 hrs 4.2.84 |
| 1745 hrs | Awoken by alarm having sleep well | 0745 hrs |
| | RETURN JOURNEY | |
| 0930 hrs 19.2.84 | Arrived Melbourne | |
| | Spent day around the house | |
| 2250 hrs | Took Capsule B, fell asleep | |
| 0515 20.2.84 | Awoke after good sleep. Took Capsule B but could not go to sleep again | |
| | Felt extremely tired in the evening | |
| 2230 hrs | Took Capsule B, fell asleep | |
| 0230 hrs 21.2.84 | Awoke, took Capsule B, fell asleep again | |
| | Felt extremely tired in the evening | |
| 2250 hrs | Took Capsule B, fell asleep | |
| 0640 hrs 22.2.84 | Slept well, awoken by alarm | |
| | Felt extremely tired late in the evening | |
| 2400 hrs | To bed, took Capsule B. Restless sleep | |
| 0320 hrs 23.2.84 | Awoke, took Capsule B | |
| 0640 hrs | Awoken by alarm | |

COMMENT

Before being told which was the active substance and which the placebo, the subject concluded that Capsule A had had and effect in making him less tired and more alert in the meetings at WHO in Geneva. In contrast, he feld that Capsule B had had no effect since he was as tired as usual on returning to Melbourne. This was the correct diagnosis. This example shows melatonin's ability to rapidly entrain a subject to a new time zone. Within 24 hours of entering a new time zone Subject B was able to sleep during a period that coincided with early morning in the zone of departure.

EXAMPLE 6

Subject C—Flight from Melbourne→Los Angeles→Washington→London→Vancouver→Melbourne 15.2.84–27.3.84

The subject, a Professor who had never taken Melatonin before, was given gelatin capsules containing 5 mg Melatonin and instructed to take one capsule on going to bed in the evening (local time) after arrival at his destination, and to take a further capsule if he awoke in the night.

The following is a verbatim account of the subject's impressions:

"The first use of Melatonin followed an uninterrupted flight from Melbourne to Los Angeles, arriving Los Angeles 9.00 am. That night I took one capsule on retiring and a second when I awoke during the night. The sleep that night appeared normal; it is my normal habit to awake most nights. The following day I felt very close to normal. The next night in Los Angeles my sleep was normal without taking any more capsules.

Following a flight from Washington to London which involved a five hours time-zone change I arrived in London mid-morning and felt tired enough that I fell asleep that afternoon. That evening I took one capsule on retiring and on awakening during the night took a second capsule. I awoke next day feeling normal and appeared to be fully adjusted to the London time on that and the following day.

An uninterrupted flight from London to Vancouver involved a time-zone change of eight hours. I arrived at Vancouver in the evening. Again I took one capsule on retiring and another when I awoke during the night. The next day I felt a little unusual and later, around 4.00 pm felt very sleepy, perhaps as if still partly on "London time". The following night I had a normal sleep and on the next day felt fully adjusted to Vancouver time.

Overall, my subjective feeling was that the Melatonin made a great improvement over my normal experience of jet-lag. On flights such as those listed above I normally feel very peculiar, a kind of unreal feeling. It usually takes me two or three days to settle into the new sleeping and waking pattern. However the marked improvement in my response to time-zone changes that was brought about by using the Melatonin capsules enabled me to work quite effectively immediately following arrival in the new location. It was such a contrast to previous experiences that I would be anxious to make use of further Melatonin tablets in this way on any future trips involving substantial east-west travel."

COMMENT

Subject C found that melatonin prevented the usual, unpleasant symptoms associated with rapid changes in time zones. This Subject undoubtedly gained considerable benefit from entrainment with melatonin and the method of the present invention.

EXAMPLE 7

Subject D—Flight from Melbourne→London→Edinburgh→London→Melbourne 23.3.84–2.4.84

The subject a Clinical Professor who had never taken Melatonin before, was given gelatin capsules containing 5 mg Melatonin and instructed to take one capsule on going to bed in the evening (local time) after arrival at his destination, and to take a further capsule if he awoke in the night.

The following is a verbatim account of the subject's impressions:

"I am writing informally to let you know of my experience using melatonin (capsules, 5 mg) as a hynotic/regularizer of diurnal rhythms, on a recent (Mar. 23–April 2) trip to and from Edinburgh.

On the outward leg, in retrospect, I took melatonin at the wrong time. The flight (Melbourne-Perth-Bombay-London) left here at 1925: I worked Melbourne-Perth, slept very soundly without taking anything Perth-Bombay, and took 5+5 mg on the Bombay to London leg. As this was morning, Melbourne time, and I had slept soundly already, I slept little if at all on this leg. I was, however, able to work effectively in reviewing a series of manuscripts for journals.

Having arrived in London at 1030 GMT I felt slightly sleepy at around 1600, and slept deeply until approximately 1930 in a day-bed at a friend's house. I dined, shared a bottle of wine, talked with friends until midnight, took 5 mg of melatonin and slept soundly until 0630 GMT (0730 summer time, the changeover having been effected during the night).

I took melatonin 5 mg on each of the three succeeding nights, and enjoyed 6-6½ hours excellent sleep. I napped minimally during the talks at the British Endocrine Societies meeting, certainly much less than when using Mogadon as an hypnotic, and no more than during a local meeting with no problem of jet lag.

I discontinued melatonin for the last two nights, with no adverse efiects, and 6-6½ normal sleep duration) hours of sleep each night. On the return trip (Edinburgh-London-Muscat-Singaport-Sydney-Melbourne) I catnapped on the shuttle between Edinburgh (departure 1940) and London, and worked without sleeping London-Muscat-Singapore. After Singapore (approximately 10 a.m. Edinburh time, approximately 100 a.m. Melbourne time) I took 5 mg melatonin, and slept for approximately 4 hours.

I dozed for 30 minutes as a passenger on a car ride on the day I arrived home, in the afternoon; apart from that I have not felt sleepy, even after a couple of glasses of wine. I have taken 5 mg each night at approximately 11.30, and have slept very satisfyingly until woken by an alarm at 6.30 a.m. On the return leg, perhaps due to delaying sleep until the appropriate time in the city of arrival, I have had absolutely no problems of jet lag; on the outward trip they were present, but much less than either untreated or when I have used Mogadon in an attempt to regularize sleep patterns.

Though I realize that this trial was not blind, I am personally convinced of the efficacy of melatonin in easily and painlessly allowing me to adjust to a new time zone, sleeping at the appropriate local time and remaining awake at other times. This is in marked contrast with my previous behaviour; I would be very grateful if melatonin could continue to be made available to me on further long trips."

COMMENT

Although this subject undoubtedly gained considerable benefit from administering Melatonin in accordance with the method of the present invention, it is interesting to note that the Melatonin did *not* induce sleep when taken on the outward journey following a normal sleep period by Melbourne time. This once again suggests that the beneficial effects of Melatonin in the prevention of jet-lag cannot be attributed solely to its weak hypnotic or tranquillising role. It seems to have a more fundamental action in re-entraining the body's own sleep-wake rhythm. The experiment discribed in this example also demonstrates the superiority of the use of melatonin as herein described over traditional pharmacutical treatments such as the Mogadon.

EXAMPLE 8

Subject E—Flight from
London→Melbourne→London 30.12.83–16.1.84

The subject, a 13 year old schoolgirl who had never flown across time zones or taken Melatonin before, arrived in Melbourne on the morning of 31.12.83 feeling fairly fresh but had a sleep in the afternoon. On going to bed at 2100 hrs Melbourne time, she took 5 mg Melatonin and awoke at 0700 hrs the following morning after an excellent night's sleep. She appeared alert and active all the following day, with no symptoms of jet-lag, and again took melatonin on going to bed at 2130 hrs, slept well, and awoke at about 0700 hrs the following morning. Once again, she showed no signs of jet-lag on the 3rd day, and the same procedure was repreated on the 4th day.

On the return journey to London, she was given no Melatonin to take. Subject E, and a medical practitioner both reported that she had very great difficulty in readjusting her sleep-wake rhythm to London time after her return. She did not feel back to normal for almost a week.

COMMENT

It is generally accepted that the adverse effects on circadian rhythms caused by Westerly flights are considered to be less severe than those caused by Easterly flights.

It is interesting that in this example Melatonin appeared to prevent all symptoms of jet-lag following a flight in an Easterly direction by a young girl who had never before experienced jet-lag. However, the symptoms were abundantly evident both subjectively and objectively after her return Westerly flight, when she did not take any Melatonin.

EXAMPLE 9

Subject A 23.2.84

Figure 2:
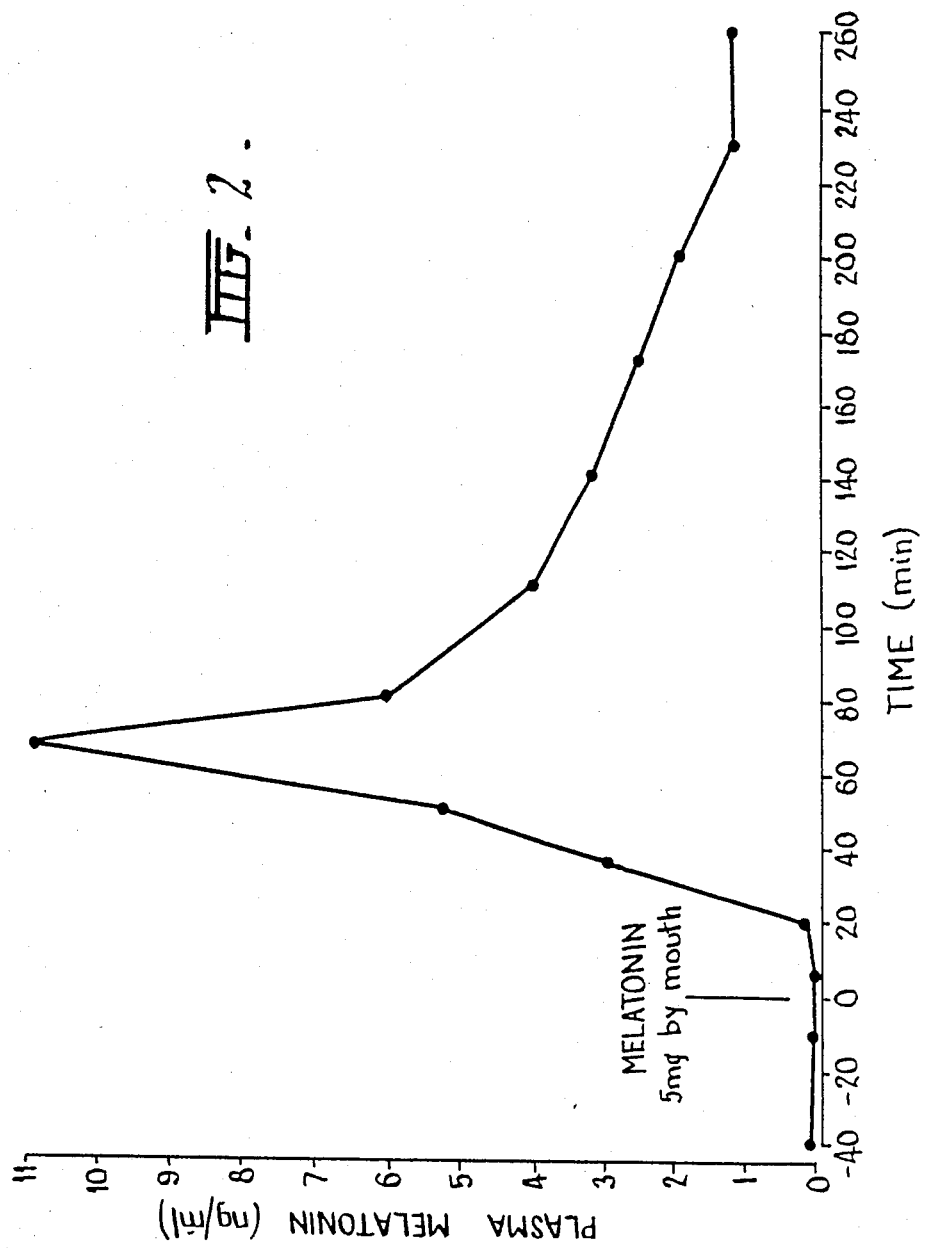
FIG. 2 is a graphical representation of the blood level of melatonin as a function of time before and after swallowing 5 mg. melatonin in a gelatin capsule.

In order to investigate the rate of absorbtion and the clearance of orally administered melatonin, and the blood levels that are achieved, Subject A had an indwelling catheter inserted in the antecubital vein of his left arm at 0900 hrs and 5 ml blood samples were withdrawn into a heparinised syringe at frequent intervals before and after swallowing 5 mg Melatonin in a gelatin capsule. This was two hours after a light breakfast of apple juice, cereal and tea. Blood sampling was continued until 1400 hrs. The blood was immediately centrifuged, and the plasma frozen until assayed for melatonin using a specific radioimmunoassay developed in the inventors' laboratory as a modification of the procedure originally described by D. J. Kennaway et al. (Endocrinology 110, 1766, 1982.) The results are shown in the accompanying FIG. 2.

The basal melatonin values in the first two samples were slightly higher than the expected normal diurnal values of around 50 pg/ml plasma. The plasma concentrations did not start to rise until 20 min after ingestion of the capsule, and the peak concentration, which was 100 times higher than the pre-ingestion basal values was achieved 66 minutes after ingestion. The values then fell, although 260 minutes after ingestion they were still 10 times higher than the normal nocturnal values than one might expect to find of around 100 pg/ml plasma. It was interesting that subjective feelings of drowsiness were experienced when the melatonin concentration first exceeded 2 ng/ml, with yawning and sleepiness coincident with the maximal levels.

If pharmacological blood levels of melatonin are necessary for re-entrainment of circadian rhythms and for inducing sleep, there would be an advantage in prolonging the time for which blood levels are elevated above 2 ng/ml. Maintaining such levels should prevent the problem of waking-up 4 hours during melatonin induced sleep as was the experience of most of the subjects studied.

This experiment does demonstrate that when ingested melatonin rapidly reaches a high plasma level the peak level is achieved within 60 minutes. However, the peak level is not maintained as it is also rapidly metabolised. This experiment clearly demonstrates the need for formulating melatonin into a slow release form. By administration of melatonin in a slow release form it will be possible to maintain high plasma levels for the whole sleep period.

The method of the present invention may be enhanced by using melatonin combined with a known slow release pharmaceutical carrier.

EXAMPLE 10

Subject F—Simulated conditions of rapid rotating shift work roster.

15.1.84–8.2.84.

The subject was a 38 year old male psychology lecturer who had never taken Melatonin before. In order to evaluate the effects of Melatonin on adaptation to rotating shift work conditions the subject undertook three, eight hour phase advances in his sleep-wake/work-rest schedule at six day intervals. Melatonin was administered under double blind conditions on the first phase advance and placebo taken on the second. In marked contrast to the placebo condition there was good and accelerated entrainment of the body temperature rhythm due to Melatonin administration. This entrainment was not a secondary consequence of sleep induction. The data can be taken as evidence for Melatonin as an effective chronobiotic for adaptation to shiftwork.

The following constitutes the main aspects of the method and results of the study.

The experiment was designed to incorporate the salient features of a rapidly rotating shift-work schedule combined with aspects of lighting changes encountered on destination arrival after intercontinental jet flight. The experiment involved five stages: pre-baseline (7 days); stage A, baseline (4 days); stage B, first 8 hour advance of darkness (6 days); stage C, second 8 hour advance of darkness (6 days), and stage D (6 days), a third 8 hour advance of darkness and hence return to baseline conditions. The experimental protocol differed from that normally found in shift work in that the subject had to spend the dark period in bed in an isolation unit irrespective of whether sleepiness was felt or not; whereas, no sleep was allowed during the light period no matter how tired the subject felt. During the light period the subject was free to leave the isolation unit to engage in work or leisure related activities. An example of details of a daily activity schedule taken from a diary is shown in Table 2.

The experiment was carried out over the long vacation, the isolated unit being situated half below ground under one of the residential colleges on La Trobe University Campus. The area was, therefore, fairly well buffered against external noise and a ventilation exhaust fan was continuously running, which aided extraneous noise reduction. Windows located high up on the walls of a kitchen alcove and shower/toilet rooms were blacked out. The main sleeping-living room was illuminated by two fluorescent tubes (40 watt) while the alcove and bathroom area had one, 40 watt, fluorescent light in each. All lights were controlled by a single time clock set to give an LD 16:8 cycle, lights on at 0730 hours during baseline. A bedside lamp was used for reading during the light period. No lighting was allowed during the dark period for any reason. Therefore, events such as quenching of thirst and urination had to take place in total darkness. Temperature of the isolation area was maintained within the range 20°-22° C. throughout the experiment. During stage A and pre-baseline breakfast was ingested between 0800 and 0900, lunch between 1300 and 1400) and dinner between 1800 and 2000. During stages B and C meals and intermeal intervals were scheduled for equivalent times (relative to lights on) to those during stage A.

During stages B and C the subject was instructed to take one capsule just prior to lights off. If still awake one hour later, the subject was to take a second capsule. Similar instructions applied to the second and third hours after lights-off but no capsule was to be taken during the last four hours of darkness i.e. maximum number of capsules to be taken was four. Capsules were refrigerated and had to be taken in complete darkness once lights were off. A double blind procedure was employed with stage B being drug (Melatonin, Sigma, 5mg/capsule) and stage C being placebo (sucrose filled capsule). No capsules were taken on the final dark period at the end of each stage i.e. days 10 and 16.

Rectal temperature was sampled every 12 minutes using a Vitalog PMS 8 portable microcomputer. A diary of life events was kept. These included details of sleep, work, leisure, meals, beverages, urination and defecation.

During baseline a clear sinusoidal, daily rhythm in rectal temperature was recorded, with the nadir of the rhythm occurring either at the middle or towards the end of the dark period. The rhythm was obscured on the first day on the phase shift (day 5) and missing data on day 7, due to battery failure, make it hard to envisage the development of the entrainment pattern. Nevertheless, by the third complete day after the phase shift (day 8) the temperature rhythm was reestablished and in phase with the new light-dark cycle. This is remarkably quick re-entrainment, especially considering the fact that (a) the external cycle of night and day and (b) social entrainment factors are both competing with the entrainment capacity of artificial LD cycle. The decrease in body temperature during the dark period was not a secondary, exogenous effect of melatonin-induced sleep since the same temperature waveform was seen on day 10 when no malatonin was taken. Furthermore from diary descriptions, it was clear that melatonin did not have the same potent sleep induction as reported by other subjects after intercontinental flight. It was only in retrospect, after placebo treatment, that melatonin's sleep, tranquility properties emerged. Therefore, in stage A, Melatonin phase shifted the rectal temperature rhythm and aided sleep induction.

In stage B and same phenomena were not seen for placebo treatment. The clear waveform demonstrated for baseline and days 8, 9 and 10 of Melatonin contrast markedly with the erratic pattern under placebo conditions. In the placebo conditions a strong exogenous (masking) component is found. By day 15 the body temperature rhythm has phase delayed back to the original baseline pattern. The peak therefore now coincides with the new dark period. Sleep and bed rest at the peak of the rhythm produces a secondary trough thereby obscuring the peak. This phenomenon is quite marked on days 15 and 16. This interpretation is consistent with the fact that on the first day of the third phase shift (days 16/17) when the subject returned to the original baseline light dark cycle, the daily temperature rhythm *immediately* re-entrained.

These findings indicate that exogenous melatonin administration can entrain a subject's body temperature rhythm to rotating shift schedules under artificial light dark conditions despite competition from more dominant entraining agents such as the natural environmental cycle of night and day and periodic social factors. It is predicted that a combination of melatonin treatment, taken at dark onset, with beta blockers taken at beginning of light onset or with high artificial light levels (+2,000 Lux) would enhance melatonin's phase shifting of circadian rhythms. Even without these combinations, melatonin will be useful for aiding adjustment of both rotating and permanent night shift workers to their routines.

TABLE 2

Daily diary of events for (22.1.84) the first complete day after first phase shift.

| Date | Time | Location and Activity |
|---|---|---|
| 21.1.84 | 2332 | Awoke to radio and got up just after lights on. |
| " | 2350 | Urinated (120 ml) Made breakfast - cereal, 4 pieces of bread with blackberry jam; mug of tea with 2 sugars. |
| 22.1.84 | 0140 | Removed rectal probe; went to toilet but constipated; had shower. |
| | 0205 | Walked across campus to office. Worked at desk. |
| | 0235 | Black coffee with 2 sugars. |
| | 0330 | Went to Behavioural Sciences building to work on computer. |
| | 0445 | Walked back to isolation unit to cook lunch (a little late). Had 4 sausages, 2 eggs and 2 pieces of bread. |
| | 0535 | Urinated (90 ml) |
| | 0615 | Did crossword |
| | 0640 | Urinated (80 ml) Did washing in College laundry and read book. |
| | 0725 | Very bad gut ache. Went to toilet. Worked in isolation unit - reading and writing. |
| | 0915 | Urine 80 ml. |
| | 0925 | Drove to Northcote to visit friends. |
| | 1030 | Coffee with 2 sugars Went for walk |
| | 1230 | Steak Sandwich (big one) for dinner Coffee with 2 sugars Drove back to isolation unit |
| | 1335 | Urinated 250 ml. |
| | 1400 | Sat in sun but too hot so came back indoors. |
| | 1420 | Coffee (decaffinated) with 2 sugars. |

TABLE 2-continued

Daily diary of events for (22.1.84) the first complete day after first phase shift.

| Date | Time | Location and Activity |
|---|---|---|
| | 1435 | Sitting in chair feeling very sleepy. Too tired to read manuscript. J.R. arrived to check that all is well. |
| | 1515 | J.R. left. Cleaned my teeth. Took capsule. |
| | 1525 | Urinated 100 ml. Went to bed. |
| | 1530 | Lights out. Fell asleep after approx. 30 minutes. |
| | 1754 | Awoke. Urinated into container in the dark. Took second capsule from fridge. |
| | 2330 | Awoke to radio alarm one minute before lights on. Had been dreaming. Had "early morning" erection. |
| | 2344 | Urinated 460 ml. |
| | 2350 | Breakfast. |

Figure 3:
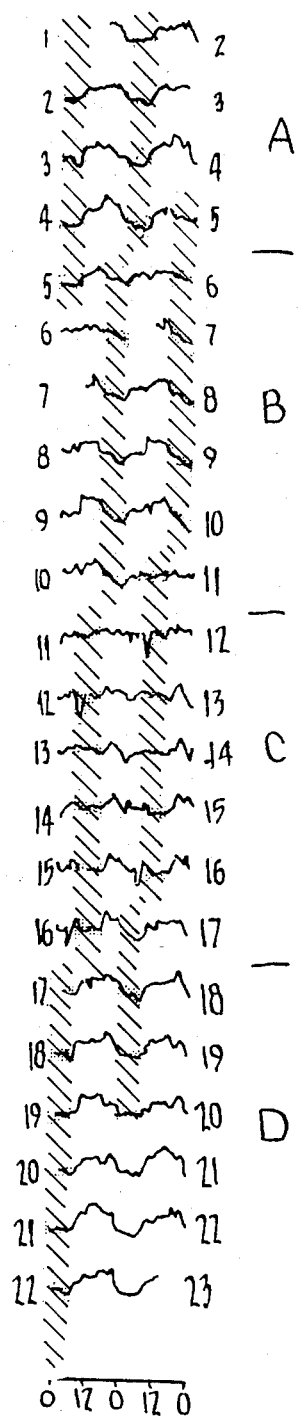
Figure 4:
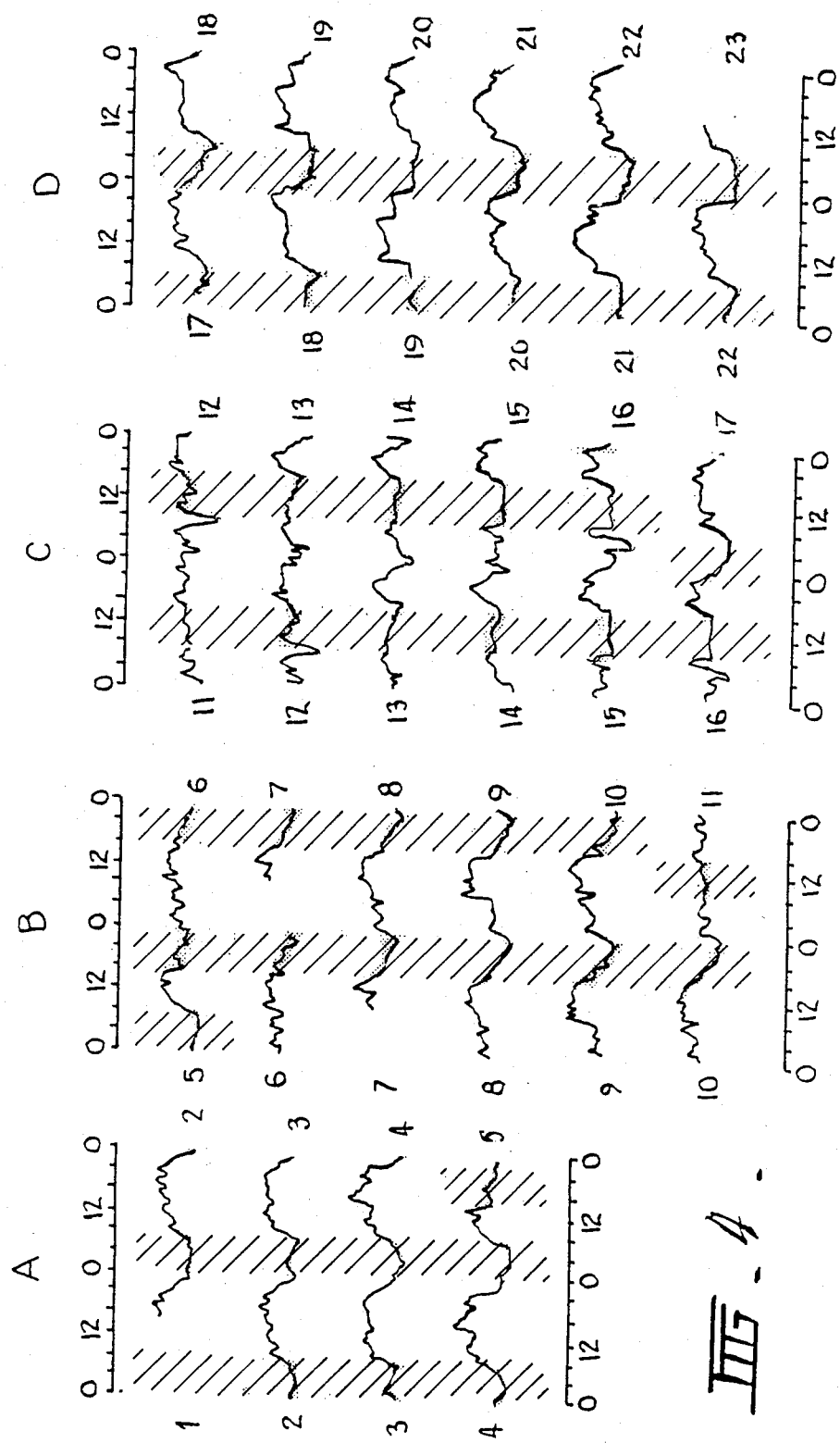

FIGS. 3 and 4 display the forty-eight hour plots of rectal temperature rhythm for subject F during the 4 stages of the experiment. The dark dotted regions represent dark periods. The numbers 1 to 23 identifies 24 hour divisions. Divisions 2 to 22 are repeated to give continuity to the record; i.e. the data is plotted over 48 hour scale in order to aid visualization of the waveform. Stage A constitutes baseline; Stage B an 8 hour advance of darkness when melatonin was taken just before dark onset and again hourly if no sleep occured; Stage C is a second 8 hour advance in darkness with placebo administration; Stage D a third 8 hour advance of darkness to come back in line with Stage A. Shaded areas indicate the 8 hours of darkness. FIG. 4 is the same as FIG. 3, but with each stage shown separately.

It will be clearly understood that the invention in its general aspects is not limited to the specific details referred to hereinabove.

I claim:

1. A method of alleviating the effects of disturbed circadian rhythms on bodily performance and function in a human subject comprising administering orally to said subject melatonin at a time when the subject's sleep cycle should commence, the amount of melatonin being sufficient to re-entrain the disturbed circadian rhythms of said subject.

2. A method of entraining circadian rhythms to a predetermined cycle having a periodicity of approximately 24 hours in a human subject comprising administering orally to said subject melatonin at a time which coincides with the sleep phase of the predetermined cycle, the amount of melatonin being sufficient to entrain the circadian rhythms to said predetermined cycle.

3. A method according to claim 2 wherein said oral administration is maintained at approximately 24 hour intervals at least until the subject's circadian rhythms have been entrained to the predetermined cycle.

4. A method of alleviating the effects of disturbed circadian rhythms due to undergoing a rapid change in time zones comprising administering orally to a human subject melatonin at a time when the subject's sleep phase should occur in a predetermined time zone, the amount of melatonin being sufficient to re-entrain the disturbed circadian rhythms of said subject.

5. A method of alleviating the effects on circadian rhythms of a rapid transition from one time zone to any number of ther time zones in a human subject comprising administering orally to said subject melatonin at a time chosen to be the subject's sleep phase, the amount of melatonin being sufficient to alleviate the effects on circadian rhythms of a rapid transition from one time zone to any number of other time zones.

6. A method of alleviating the effects on circadian rhythms of a rapid transition from one time zone to a second time zone in a human subject comprising administering orally said subject melatonin at a time when the subject's sleep phase should occur in the second time zone, the amount of melatonin being sufficient to alleviate the effects on circadian rhythms of a rapid transition from one time zone to a second time zone.

7. A method of alleviating the effects on circadian rhythms of rapidly altering the 24 hours routine in a human subject comprising administering orally to said subject melatonin at a time that coincides with the sleep phase within a new 24 hour routine, the amount of melatonin being sufficient to re-entrain the disturbed circadian rhythms of said subject.

8. A method of alleviating the effects on circadian rhythms of living in an environment substantially free of zeitgebers of 24 hour periodicity comprising orally administering to said subject melatonin at a time that coincides with the desired sleep phase of the subject, the amount of melatonin being sufficient to alleviate the effects on circadian rhythms of living in an environment substantially free of zeitgebers of 24 hour periodicity.

9. A method of alleviating the effects of a disturbance in the body temperature circadian rhythm in a human subject comprising administering orally to said subject melatonin in an amount sufficient to alleviate the effects of a disturbance in the body temperature circadian rhythm in a human subject.

10. A method of entraining a body temperature circadian rhythm to a predetermined cycle having a periodicity of 24 hours in a human subject comprising administering orally to said subject melatonin, the amount of melatonin being sufficient to entrain a body temperature circadian rhythm to a predetermined cycle having a periodicity of 24 hours in a human subject.

11. A method according to any of claims 1-6 and 7-10 wherein the dose of melatonin adminstered is in the range 1 to 10 mg.

12. A method according to any one of claims 1-6 and 7-10 wherein the melatonin is combined with a pharmacologically acceptable carrier.

13. A method according to any one of claims 1-6 and 7-10 wherein the melatonin is administered in a slow release form.

* * * * *

UNITED STATES PATENT AND TRADEMARK OFFICE
CERTIFICATE OF CORRECTION

PATENT NO. : 4,600,723
DATED : July 15, 1986
INVENTOR(S) : SHORT, Roger V.

It is certified that error appears in the above—identified patent and that said Letters Patent is hereby corrected as shown below:

Title page, item [75] should read as follows:

[75] Inventor: Roger V. Short
Glen Waverly, Australia

Signed and Sealed this

Twenty-first Day of October, 1986

[SEAL]

Attest:

DONALD J. QUIGG

Attesting Officer

Commissioner of Patents and Trademarks